(12) United States Patent
Mernoe et al.

(10) Patent No.: US 7,918,834 B2
(45) Date of Patent: Apr. 5, 2011

(54) DROP COUNTER

(75) Inventors: Morten Mernoe, Charlottenlund (DK); Morten Thing, Copenhagen K (DK)

(73) Assignee: T3M, Charlottelund (DK)

( * ) Notice: Subject to any disclaimer, the term of this patent is extended or adjusted under 35 U.S.C. 154(b) by 144 days.

(21) Appl. No.: 12/396,159

(22) Filed: Mar. 2, 2009

(65) Prior Publication Data
US 2009/0227939 A1  Sep. 10, 2009

Related U.S. Application Data

(60) Provisional application No. 61/034,287, filed on Mar. 6, 2008.

(51) Int. Cl.
*A61M 5/14* (2006.01)

(52) U.S. Cl. .......................... 604/253; 604/65

(58) Field of Classification Search .............. 604/65–67, 604/253; 356/442
See application file for complete search history.

(56) References Cited

U.S. PATENT DOCUMENTS

| | | | |
|---|---|---|---|
| 4,038,982 A | 8/1977 | Burke et al. | |
| 4,346,606 A | 8/1982 | Cannon et al. | |
| 4,496,351 A | 1/1985 | Hillel et al. | |
| 4,507,112 A | 3/1985 | Hillel et al. | |
| 4,525,163 A | 6/1985 | Slavik et al. | |
| 4,583,975 A | 4/1986 | Pekkarinen et al. | |
| 4,623,331 A * | 11/1986 | Cewers et al. | 604/65 |
| 4,634,426 A | 1/1987 | Kamen | |
| 4,775,368 A | 10/1988 | Iwatschenko | |
| 5,045,069 A | 9/1991 | Imparato | |
| 5,152,424 A * | 10/1992 | Weinreb et al. | 222/1 |
| 5,166,667 A | 11/1992 | Jen | |
| 5,186,057 A * | 2/1993 | Everhart | 73/861.41 |

(Continued)

FOREIGN PATENT DOCUMENTS

EP  0 321 996  6/1989

(Continued)

OTHER PUBLICATIONS

International Search Report for corresponding International Application PCT/EP2009/052478 mailed Jun. 5, 2009.

*Primary Examiner* — Nicholas D Lucchesi
*Assistant Examiner* — Gerald Landry, II
(74) *Attorney, Agent, or Firm* — Merchant & Gould P.C.

(57) ABSTRACT

A liquid flow control system for use with infusion sets of the type comprising a liquid supply, a drip chamber 8 downstream of the liquid supply for forming liquid drops and a flexible tube 7 connecting the drip chamber with an injection needle, the system comprising a drop sensor 4 adapted for being arranged adjacent the drip chamber for sensing the passage of drops through the drip chamber, a valve 19 adapted for controlling the flow of the liquid through the tube, valve activating means for activating the valve, electrical circuits for registering the rate of drop formation and controlling the valve activating means, and a battery for powering the drop sensor, the electrical circuits and the valve activating means, the drop sensor, the valve, the valve activating means, the electrical circuits and the battery being mounted on or in a common housing having housing attachment means for releasably attaching the housing to the flexible tube.

21 Claims, 5 Drawing Sheets

U.S. PATENT DOCUMENTS

| | | | |
|---|---|---|---|
| 5,415,641 A * | 5/1995 | Yerlikaya et al. | 604/251 |
| 5,439,442 A * | 8/1995 | Bellifemine | 604/65 |
| 5,938,543 A | 8/1999 | McGeeney et al. | |
| 5,982,289 A | 11/1999 | Kingsley et al. | |
| 6,491,659 B1 | 12/2002 | Miyamoto | |
| 2008/0139997 A1 * | 6/2008 | Sacchetti | 604/67 |

FOREIGN PATENT DOCUMENTS

| | | |
|---|---|---|
| EP | 0 493 741 A2 | 7/1992 |
| EP | 0 718 001 A2 | 6/1996 |
| FR | 2 272 435 | 12/1975 |
| GB | 1 520 606 | 8/1978 |
| WO | WO 02/40084 A2 | 5/2002 |

* cited by examiner

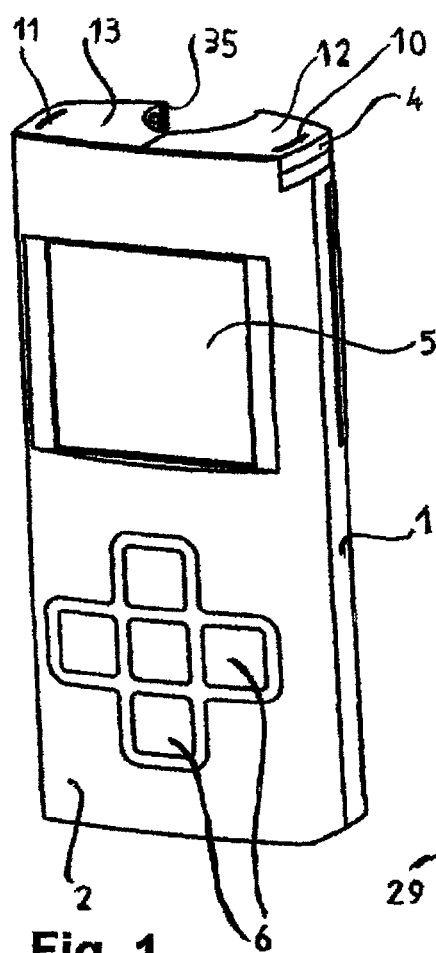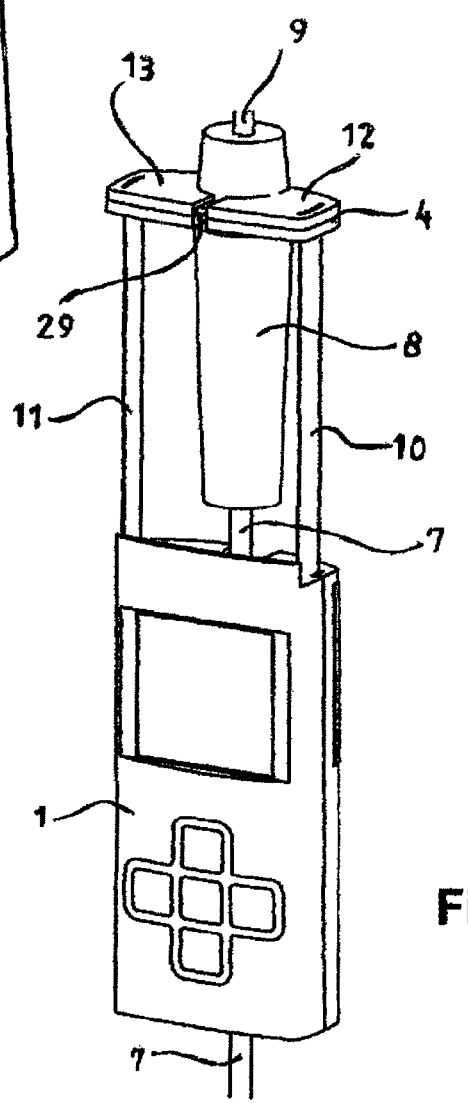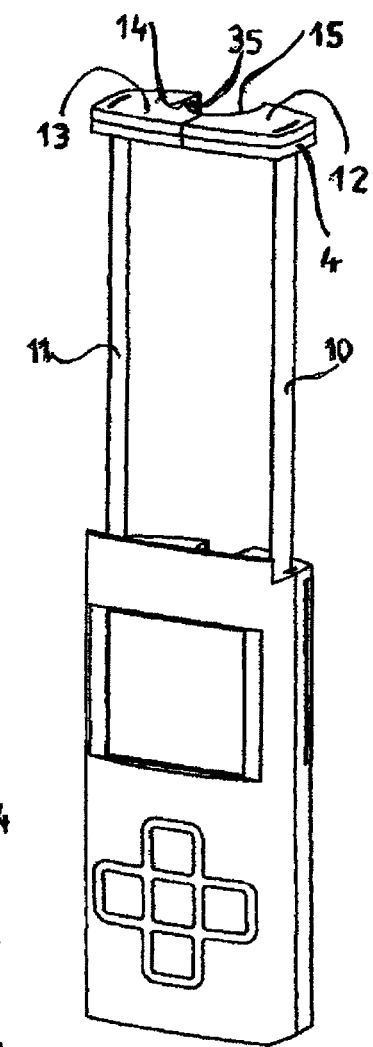
Fig. 1
Fig. 2
Fig. 3

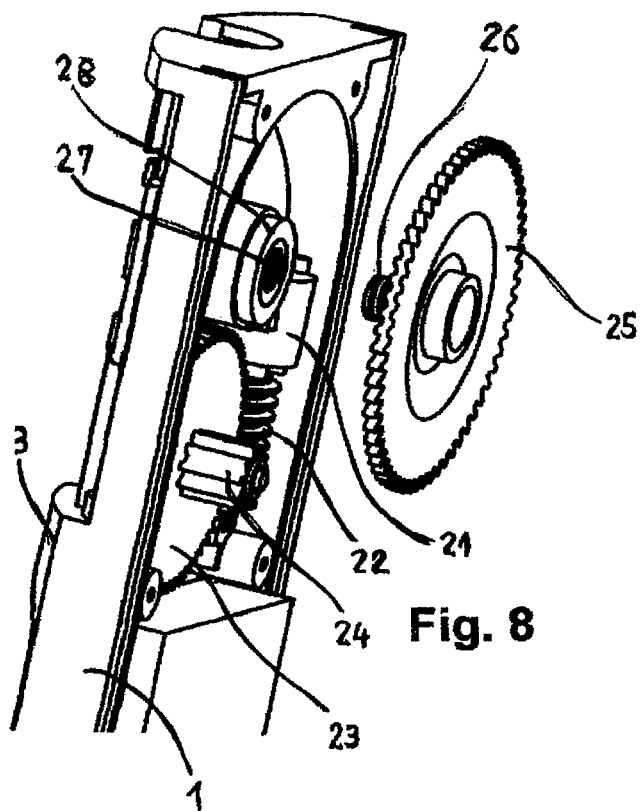
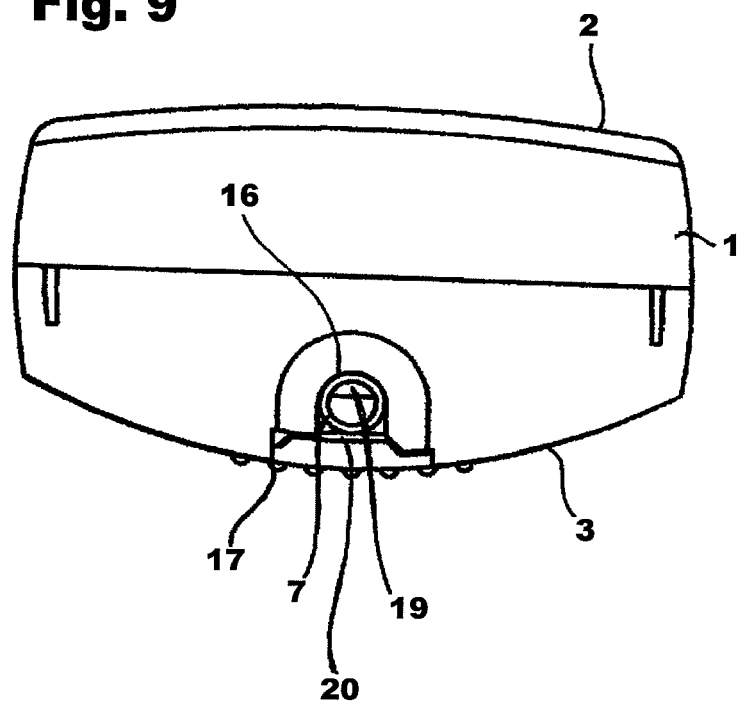

DROP COUNTER

This application claims the benefit of Ser. No. 61/034,287, filed Mar. 6, 2008 in the United States and which application(s) are incorporated herein by reference. A claim of priority to all, to the extent appropriate is made.

BACKGROUND

The present invention relates to a liquid flow control system for use with infusion sets of the type comprising a liquid supply, a drip chamber downstream of the liquid supply for forming liquid drops and a flexible tube connecting the drip chamber with an injection needle, the system comprising a drop sensor adapted for being arranged adjacent the drip chamber for sensing the passage of drops through the drip chamber, a valve adapted for controlling the flow of the liquid through the tube valve activating means for activating the valve, electrical circuits for registering the rate of drop formation and controlling the valve activating means, and a battery for powering the drop sensor, the electrical circuits and the valve activating means.

In connection with infusion sets it is known to monitor the rate of formation of drops in a drip chamber by means of drop sensors connected to programmable controllers that can calculate the rate of drop formation and compare it with a set value. Such systems are disclosed in U.S. Pat. No. 5,938,543, U.S. Pat. No. 5,045,069, U.S. Pat. No. 4,346,606 and U.S. Pat. No. 4,583,975, the disclosures of which are hereby incorporated herein by reference.

U.S. Pat. No. 4,634,426, U.S. Pat. No. 4,775,368 and U.S. Pat. No. 4,038,982, the disclosures of which are hereby incorporated herein by reference, disclose drop monitor means connected to a controller that again is electrically connected to a separate valve means or occlusion means attached to the flexible tube leading from the drip chamber to the infusion needle of the infusion set. The valve means or occlusion means vary the flow of liquid through the flexible tube so that the set rate of drop formation can be complied with.

As the liquid flow control systems known in the art thus comprise 2-3 separate individual units interconnected by electrical wires and needing to be mounted separately, the known systems are difficult to apply to the infusion sets, the connecting wires may become entangled with other objects or disconnected entailing failure of the system, and the mounting procedure is prone to errors leading to malfunction of the system.

SUMMARY

One of the objects of the present invention is to provide a liquid flow control system of the type in reference that is totally self-contained, that has no loose wires, and that can be attached to different types of infusion sets with greatly reduced risk of errors.

This object is achieved by the drop sensor, the valve, the valve activating means, the electrical circuits and the battery being mounted on or in a common housing having housing attachment means for releasably attaching the housing to the flexible tube.

Hereby, a sole unit is to be attached, and the operator does not have to remember a series of instructions when mounting the unit.

Although various drop sensing systems can be used in connection with the control system according to the invention, it is currently preferred that the drop sensor comprises a light beam emitter for emitting a light beam and at least two light sensors arranged for co-operating with said light beam emitter such that an alteration of said light beam by a drop in said drip chamber is sensed by at least one of said light sensors. Hereby a greater security of sensing the passage of a drop through the drip chamber is achieved even though the drip chamber should be inclined so that the drop does not fall along the axis of the cylindrical drip chamber.

Preferably the frequencies of the light of the light beam lie within a relatively narrow range and the light sensors are adapted for only sensing light with frequencies lying within said narrow range. Hereby, the possibility of extraneous variations of the light or conditions outside the drip chamber influencing the light sensors so as to cause errors in the drop count is reduced.

In the currently preferred embodiment at least one of said light sensors is located such that it is illuminated directly by light from said light beam.

In the currently preferred embodiment a straight line extending between said light beam emitter and a light sensor illuminated directly by said light beam forms an acute angle with the axis of said light beam, said angle preferably being between 0 and 30 degrees, more preferably between 5 and 25 degrees, even more preferably between 10 and 22 degrees and most preferably between 15 and 20 degrees, for instance 17.5 degrees.

Advantageously, at least one of said light sensors is located such that it is not illuminated directly by light from said light beam but can sense light from said light beam reflected from a drop passing through said drip chamber. This affords greater security of registering the passage of a drop even though the drip chamber is inclined to such a degree that a directly illuminated light sensor does not sense a shadow of the drop.

In the currently preferred embodiment the light beam emitter and the light sensors are arranged on a first and a second body, said first and second bodies being connected to one another such that the distance between them is variable so as to enable said bodies to be placed adjacent the periphery of drop chambers with different diameters.

In the currently preferred embodiment the light emitter is mounted on said first body and light sensors illuminated directly by light from said light beam are mounted on said second body.

In an alternative embodiment, the light emitter is mounted on said first body and a light sensor illuminated indirectly by light from said light beam reflected from a drop passing through said drip chamber is mounted on said first body.

In the currently preferred embodiment one of said two bodies is mounted on a rod or arm that is received longitudinally displaceable in the other of said bodies, and a biasing means is provided for biasing said two bodies towards each other such that said two bodies and said biasing means form a clamping means for clamping said drop sensor to the surface of said drip chamber.

In the currently preferred embodiment the housing comprises length adjustable carrier means for carrying said drop sensor, said length adjustable carrier means comprising two generally rectilinear and mutually parallel, telescopically extendable and retractable rods or arms. Hereby, the housing can be releasably attached to the flexible tube without having to take undue consideration of the distance from the housing to the drip chamber as the length of the carrier means can be adjusted to compensate for different such distances between the housing and the drip chamber.

Preferably, the arms are arranged longitudinally displaceable in channels in said housing, each of said channels preferably being located at one of two opposed edges of said housing, and the body is carried by one of said rods or arms and said second body is carried by the other of said rods or arms.

In a further aspect, the present invention relates to a drop sensor for use in a liquid flow control system for use with infusion sets of the type comprising a liquid supply, a drip chamber downstream of the liquid supply for forming liquid drops and a flexible tube connecting said drip chamber with an injection needle, said drop sensor being adapted for being arranged adjacent said drip chamber for sensing the passage of drops through said drip chamber, wherein said drop sensor comprises a light beam emitter for emitting a light beam and at least two light sensors arranged for co-operating with said light beam emitter such that an alteration of said light beam by a drop in said drip chamber is sensed by at least one of said light sensors.

BRIEF DESCRIPTION OF THE DRAWINGS

In the following, the invention will be explained more in detail in connection with various embodiments thereof shown, solely be way of example, in the accompanying drawings, where:

FIGS. 1-3 are schematic, perspective views of the currently preferred embodiment of a self-contained flow control system unit according to the invention in different situations, FIG. 8 is a schematic, perspective, partly exploded view of the activating mechanism of the valve for controlling the rate of liquid flow, FIG. 9 is a schematic enlarged scale view of the top of the housing of the flow control unit with the drop sensor removed.

DETAIL DESCRIPTION OF THE DRAWINGS

Figure 4:
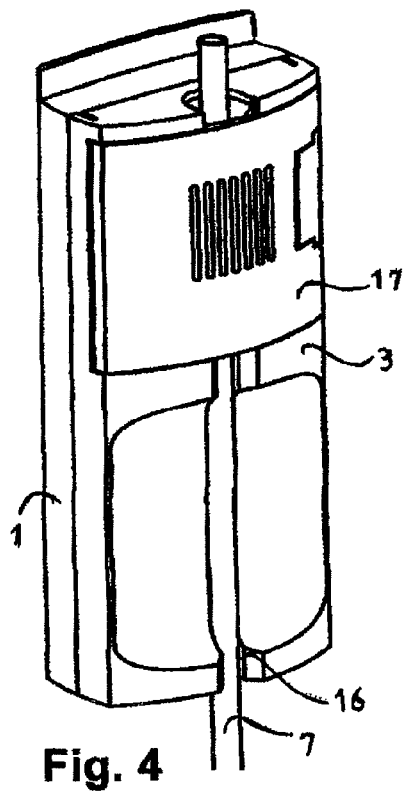
FIGS. 4-7 are schematic perspective views of the rear side of the unit with a door covering an interior chamber in the unit closed (FIG. 4) and open (FIGS. 5-7) with the drop sensor removed for the sake of clarity.

Referring now to FIGS. 1-5, a liquid flow control system unit for use with an infusion set comprises a housing 1 having a front side 2 and a rear side 3. A drop sensor unit 4 is arranged at the top of the housing 1. A display screen 5 and input keys 6 are provided in the front side 2.

Figure 5:
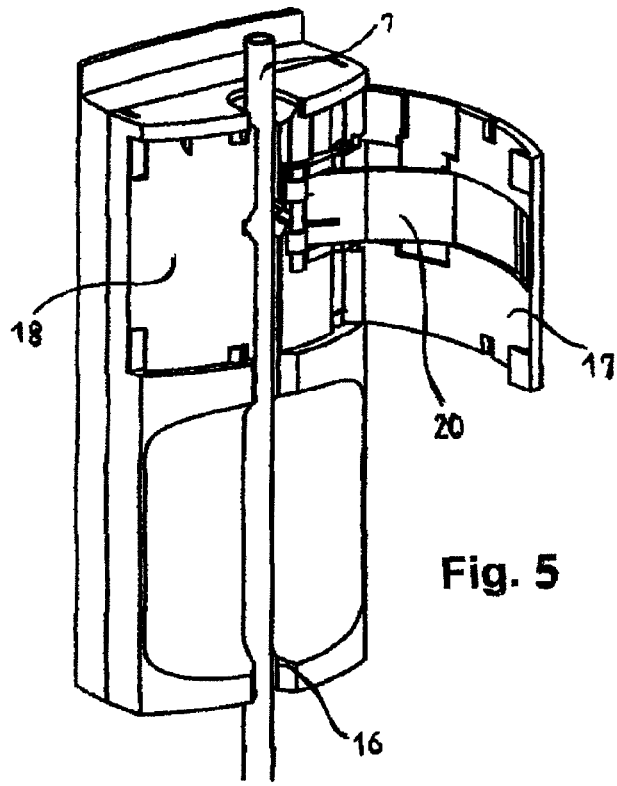

In FIGS. 3-5 the unit is shown attached to a flexible tube 7 of an infusion set of a type well known in the art having a drip chamber 8 with a transparent wall. The drip chamber 8 is connected to a not shown liquid container by means of a conduit 9, and the flexible tube 7 communicates the drip chamber 8 with a not shown injection needle for infusing the liquid into a patient using the infusion set.

As shown in FIGS. 2 and 3, the drop sensor 4 is carried by two flexible rods or arms 10 and 11 that are slidably attached in the housing 1. As described more in detail below in connection with FIGS. 10-12, the drop sensor 4 comprises two bodies 12 and 13 attached to an end of the rods 10 and 11, respectively. The rods are made of steel and have a concave cross section much like the retractable steel measuring tapes.

The bodies 12 and 13 have arcuate surfaces 14 and 15, respectively, for contacting and receiving the outer circular surface of the transparent wall of the drip chamber 8 as described more in detail below.

Referring now to FIGS. 4-9, the rear side 3 is provided with a channel or groove 16 in which the flexible tube 7 can be received when the flow control unit is to be attached to the tube 7. A hinged door 17 covers an interior chamber 18.

A wedge 19 protrudes into the bottom of the channel 16 and is displaceable to and fro towards the rear 3 of the housing 1 such that it can protrude more or less into the groove or channel 16. When the door 17 is closed and locked as shown in FIGS. 4 and 9, the flexible tube 7 is pressed against an inner surface 20 of the door 17 and against the front edge of the wedge 19 which in its position furthest from the rear 3 of the housing still protrudes into the channel 16 and presses into the flexible tube 7.

Thus, in the closed position of the door 17, the housing 1 is securely clamped to the flexible tube 7 received in the channel 16.

Referring now to FIG. 8, the displacing mechanism for displacing the wedge 19 to and fro into the channel 16 comprises a reversible step motor having its drive shaft connected to a screw or worm 22. The screw 22 meshes with a gear 23 having a pinion 24 that meshes with a gear 25 having a threaded axle 26 that engages a threaded bore 27 of a cylindrical body 28 arranged for axial movement but prevented from rotation. At an end of the body 28 furthest from the gear 25, the body 28 carries or is integral with the wedge 19.

Figure 6:
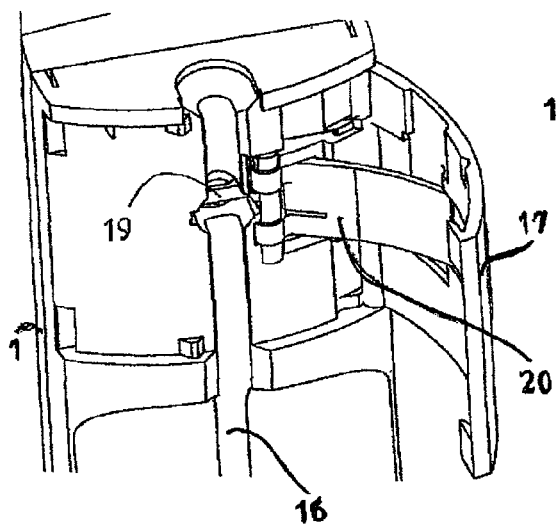
Figure 7:
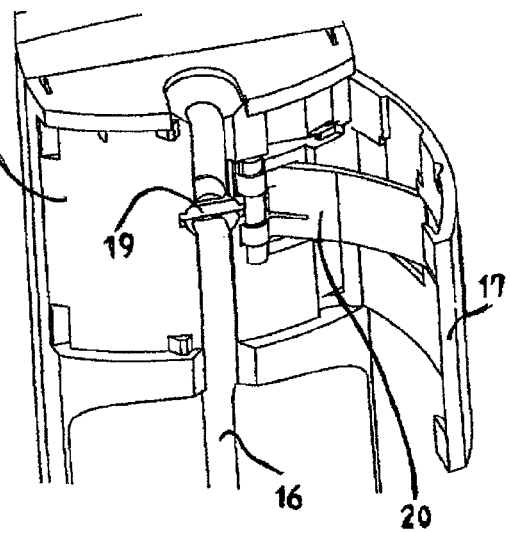

Rotation of the reversible step motor 21 in either direction will result in rotation of the gear 25 and consequently axial displacement of the body 28 whereby the wedge 19 is pressed more or less into the flexible tube 7 whereby the flow-through area of the tube 7 is reduced more or less, respectively. In FIG. 6, the wedge 19 is shown in its least protruding position, while in FIG. 7 it is shown in its most protruding position.

In an alternative embodiment, the wedge 19 may be arranged for movement parallel to the door, and the tube may be fixated in the groove by a protuberance on the inner surface of the door, the protuberance is located such that it is adjacent the wedge 19 when the door is closed so as to ensure the correct placement of the tube relative to the wedge.

Figure 10:
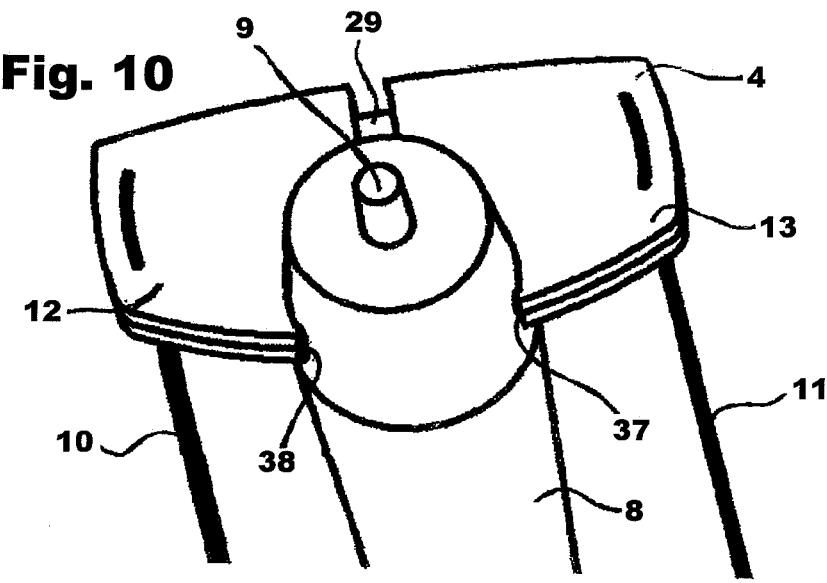
FIG. 10 is a schematic top perspective view of the drop sensor arranged on a drip chamber.
Figure 11:
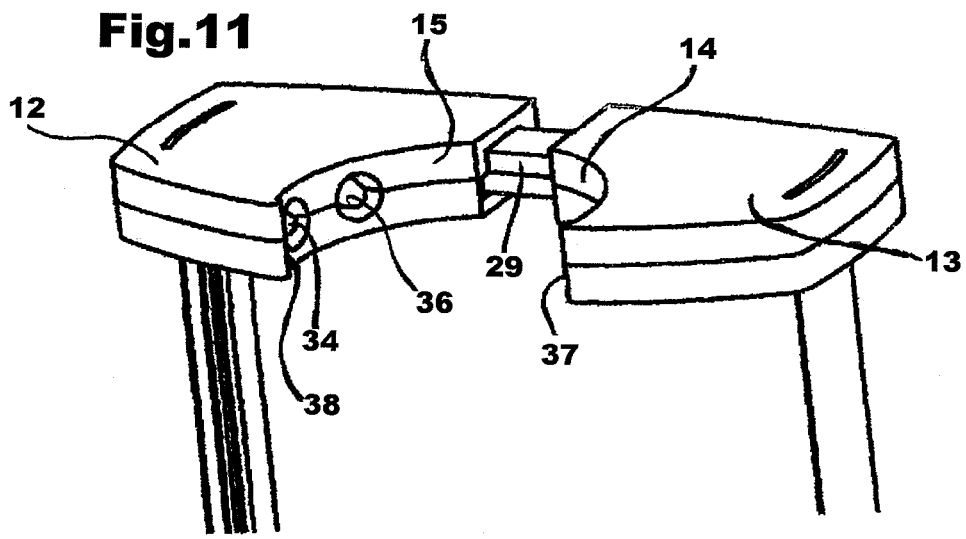
FIG. 11 is a schematic enlarged scale perspective view of the drop sensor.
Figure 12:
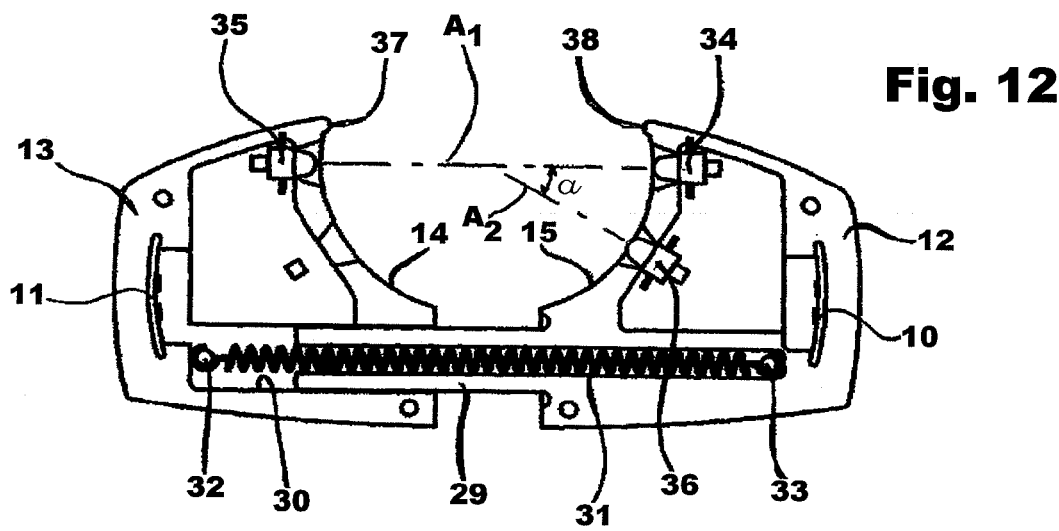
FIG. 12 is a schematic sectional top view of the drop sensor.

Referring now to FIGS. 10-12, the drop sensor 4 is shown with the bodies 12 and 13 spaced apart so as to be able to accommodate the outer surface of the drip chamber 8 between the arcuate surfaces 14 and 15.

The body 12 is provided with a rod or arm 29 that is slidingly received in a channel 30 in the body 13. A coil spring extends from a pin 32 in the body 13 to a pin 33 in the body 12 and biases the bodies 12 and 13 towards each other.

A light beam emitter 34 is arranged in the body 12 directly opposite a light sensor 35 arranged in the body 13 such that they have a common axis A1. A further light sensor 36 is arranged in the body 12. The axis A2 of the Light sensor 36 forms an acute angle a with the axis A1.

The arcuate surfaces 14 and 15 end in a ridge 37 and 38, respectively. The arcuate surfaces 14 and 15 have a curvature that entails that the positions of drip chambers with different diameters when arranged between these arcuate surfaces are such that the axis of the drip chamber approximately intersects the axis A1 with the bodies 13 and 12 contacting the surface of the drip chamber along the ridges 17 and 38, respectively, and along a vertically extending narrow area of each of the arcuate surfaces 14 and 15, respectively, such that the drops formed in the drip chamber top and falling generally along the axis of the drip chamber, will intersect the axis A1.

If a horizontal motion of the drip chamber 8 or an inclination thereof causes a drop trajectory to diverge from the axis of the drip chamber and thus not intersect the axis A1 and not be sensed by the light sensor 35, the light emitted from the light emitter 34 and reflected from the drop will be sensed by the light sensor 36 thus preventing errors in the flow rate because of drops not sensed and counted.

Figure 13:
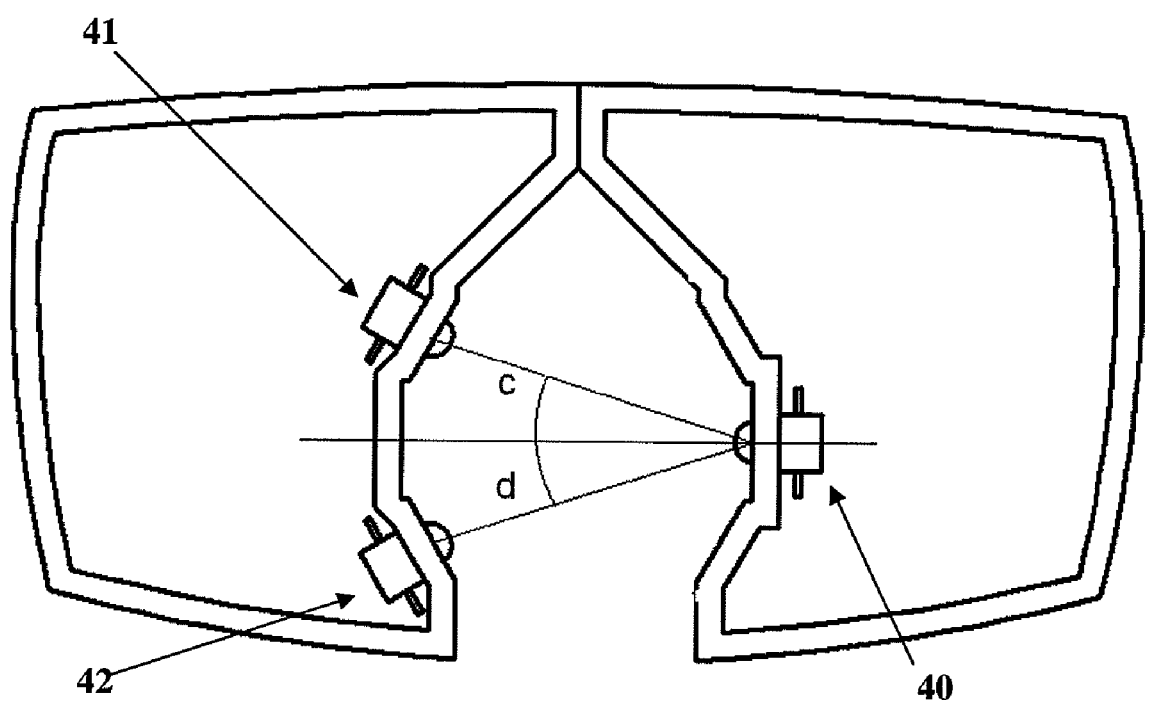
FIG. 13 is a diagrammatical view corresponding to FIG. 12 illustrating the currently preferred arrangement of the light beam emitter and two light sensors.

Referring now to FIG. 13, an alternative and currently preferred embodiment of the location of a light beam emitter 40 and two light sensors 41 and 42 is illustrated. The sensors 41 and 42 are located on one of the bodies such that they are directly illuminated by the light beam emitted by the light beam emitter 40 located on the other body. The sensors are located such that a straight line extending between the emitter 40 and each of the sensors 41 and 42 forms an acute angle c and d, respectively, with the axis of the light beam emitted by the emitter 40. The angles c and d are both currently preferred to be 17.5 degrees, but they may be different and have other values depending on the narrowness of the light beam emitted by the emitter 40.

If a drop passing down through the drip chamber arranged between the two bodies for some reason does not travel along the axis of the drip chamber such that a sensor located on the axis of the light beam would not sense the shadow caused by the drop, then either one or the other of the sensors 41 and 42 would sense the shadow caused by the drop thereby enhancing the security of the liquid control system based on the drop sensor according to the invention.

To further enhance the security of the system, further light sensors may be arranged both on the first and the second body.

Although it is believed that the efficiency of the system is best if the light beam emitter and the light sensors are arranged substantially on a common plane, arrangements where the sensors and the light beam emitter are arranged on different planes are also conceivable.

The light emitted by the light beam emitter is preferably in the infra red range and the frequencies are preferably in a narrow range of frequencies while the sensors are only able to sense light in the narrow range. Thus, the risk that extraneous influences outside the drip chamber will elicit a reaction from a sensor, for instance extraneous light sources, will be minimised.

In use, the self-contained flow control unit 1 is removed from a charging means with its battery fully charged. By means of the input keys 6, the unit is programmed to maintain a certain rate of flow characterised by the number of drops passing through the drip chamber 8 per unit of time, for instance per minute. This set rate is displayed on the display screen. Other parameters can be programmed, for instance the duration of the infusion, for instance 2 hours.

The door 17 is then opened and the flexible tube 7 extending below the drip chamber 8 of an infusion set is inserted into the channel 16 whereafter the door 17 is closed and locked. Hereby, the unit 1 is securely attached to the tube 7.

The arms or rods 10 and 11 are then extended upwards from the housing 1 until the drop sensor 4 is at the desired level relative to the drip chamber. The bodies 12 and 13 are then separated by pulling them apart against the force of the coil spring 13, and the arcuate surfaces 14 and 15 are placed around the surface of the drip chamber 8. The spring 31 will then act to fixate the sensor 4 to the surface of the drip chamber.

The infusion system is now ready for use. The drop sensor will sense the drops falling through the drip chamber, and the control circuitry will calculate the rate of drops per time unit. If the rate does not comply with the set rate the control circuitry will activate the reversible step motor to displace the wedge 19 so as to either increase the through-flow area in the flexible tube or decrease it so as to increase or decrease the rate of drops per time unit, respectively, until the set rate is complied with.

Alarms are programmed to be triggered if the set rate cannot be attained or the liquid flow stops.

The flow control unit according to the invention may be used with infusion sets with drip chambers having different diameters.

The invention claimed is:

1. A liquid flow control system for use with infusion sets of the type comprising a liquid supply, a drip chamber downstream of the liquid supply for forming liquid drops and a flexible tube connecting said drip chamber with an injection needle, said system comprising:
    a drop sensor adapted for being arranged adjacent said drip chamber for sensing the passage of drops through said drip chamber,
    a valve adapted for controlling the flow of said liquid through said tube,
    valve activating means for activating said valve,
    electrical circuits for registering the rate of drop formation and controlling said valve activating means, and
    a battery for powering said drop sensor, said electrical circuits and said valve activating means, wherein said drop sensor, said valve, said valve activating means, said electrical circuits and said battery are mounted on or in a common housing having housing attachment means for releasably attaching said housing to said flexible tube, and wherein said housing comprises length adjustable carrier means for carrying said drop sensor, said length adjustable carrier means comprising two generally rectilinear and mutually parallel, telescopically extendable and retractable rods or arms.

2. A system according to claim 1, wherein said drop sensor comprises a light beam emitter for emitting a light beam and at least two light sensors arranged for co-operating with said light beam emitter such that an alteration of said light beam by a drop in said drip chamber is sensed by at least one of said light sensors.

3. A system according to claim 2, wherein the frequencies of the light of said light beam lie within a relatively narrow range and said light sensors are adapted for only sensing light with frequencies lying within said narrow range.

4. A system according to claim 2, wherein at least one of said light sensors is located such that it is illuminated directly by light from said light beam.

5. A system according to claim 4, wherein a straight line extending between said light beam emitter and a light sensor illuminated directly by said light beam forms an acute angle with the axis of said light beam, said angle being between 15 and 20 degrees.

6. A system according to claim 2, wherein at least one of said light sensors is located such that it is not illuminated directly by light from said light beam but can sense light from said light beam reflected from a drop passing through said drip chamber.

7. A system according to claim 2, wherein said light beam emitter and said light sensors are arranged on a first and a second body, said first and second bodies being connected to one another such that the distance between them is variable so as to enable said bodies to be placed adjacent the periphery of drop chambers with different diameters.

8. A system according to claim 7, wherein said light emitter is mounted on said first body and light sensors illuminated directly by light from said light beam are mounted on said second body.

9. A system according to claim 7, wherein said light emitter is mounted on said first body and a light sensor illuminated indirectly by light from said light beam reflected from a drop passing through said drip chamber is mounted on said first body.

10. A system according to claim 7, wherein one of said two bodies is mounted on a rod or arm that is received longitudinally displaceable in the other of said bodies.

11. A system according to claim 7, wherein a biasing means is provided for biasing said two bodies towards each other such that said two bodies and said biasing means form a clamping means for clamping said drop sensor to the surface of said drip chamber.

12. A system according to claim 1, wherein said arms are arranged longitudinally displaceable in channels in said housing, each of said channels preferably being located at one of two opposed edges of said housing.

13. A system according to claim 7, wherein said first body is carried by one of said rods or arms and said second body is carried by the other of said rods or arms.

14. A system according to claim 1, wherein said housing attachment means comprises a clamping mechanism for clamping the housing to said flexible tube, and wherein said clamping mechanism comprises a channel inside a chamber in said housing covered by a door, said channel being adapted for partly receiving said flexible tube and said door being arranged such that when said door is closed said flexible tube is pressed into said channel by an inner surface of said door such that said housing is clamped to said tube.

15. A drop sensor for use in a liquid flow control system according to claim 1, wherein said drop sensor comprises a light beam emitter for emitting a light beam and at least two light sensors arranged for co-operating with said light beam emitter such that an alteration of said light beam by a drop in said drip chamber is sensed by at least one of said light sensors.

16. A drop sensor according to claim 15 wherein the frequencies of the light of said light beam lie within a relatively narrow range and said light sensors are adapted for only sensing light with frequencies lying within said narrow range.

17. A drop sensor according to claim 15 wherein at least one of said light sensors is located such that it is illuminated directly by light from said light beam.

18. A drop sensor according to claim 17, wherein a straight line extending between said light beam emitter and a light sensor illuminated directly by said light beam forms an acute angle with the axis of said light beam, said angle being between 15 and 20 degrees.

19. A drop sensor according to claim 15, wherein at least one of said light sensors is located such that it is not illuminated directly by light from said light beam but can sense light from said light beam reflected from a drop passing through said drip chamber.

20. A drop sensor according to claim 15, wherein said light beam emitter and said light sensors are arranged on a first and a second body, said first and second bodies being connected to one another such that the distance between them is variable so as to enable said bodies to be placed adjacent the periphery of drop chambers with different diameters.

21. A drop sensor according to claim 20, wherein said light emitter is mounted on said first body and light sensors illuminated directly by light from said light beam are mounted on said second body.

* * * * *